(12) United States Patent
Uihlein

(10) Patent No.: US 8,292,828 B2
(45) Date of Patent: Oct. 23, 2012

(54) GUIDE WIRE FOR A MEDICAL INSTRUMENT

(75) Inventor: Bernhard Uihlein, Dettingen (DE)

(73) Assignee: EPflex Feinwerktechnik GmbH, Dettingen/Ems (DE)

( * ) Notice: Subject to any disclaimer, the term of this patent is extended or adjusted under 35 U.S.C. 154(b) by 569 days.

(21) Appl. No.: 11/914,321

(22) PCT Filed: May 11, 2006

(86) PCT No.: PCT/EP2006/004407
§ 371 (c)(1),
(2), (4) Date: Jul. 9, 2008

(87) PCT Pub. No.: WO2006/119989
PCT Pub. Date: Nov. 16, 2006

(65) Prior Publication Data
US 2008/0312597 A1     Dec. 18, 2008

(30) Foreign Application Priority Data
May 12, 2005   (DE) .......................... 10 2005 022 688

(51) Int. Cl.
*A61B 5/00*      (2006.01)
*A61B 6/00*      (2006.01)
*A61M 5/178*     (2006.01)

(52) U.S. Cl. .................... 600/585; 600/434; 604/164.13

(58) Field of Classification Search .................. 600/585, 600/433–435; 604/163.13, 164.13
See application file for complete search history.

(56) References Cited

U.S. PATENT DOCUMENTS

| | | | |
|---|---|---|---|
| 4,771,788 A * | 9/1988 | Millar | 600/455 |
| 5,213,111 A | 5/1993 | Cook et al. | |
| 5,333,620 A * | 8/1994 | Moutafis et al. | 600/585 |
| 5,722,424 A | 3/1998 | Engelson | |
| 5,772,609 A | 6/1998 | Nguyen et al. | |
| 5,951,494 A * | 9/1999 | Wang et al. | 600/585 |
| 5,984,878 A | 11/1999 | Engelson | |
| 6,039,699 A * | 3/2000 | Viera | 600/585 |
| 6,113,557 A | 9/2000 | Fagan et al. | |
| 6,245,053 B1 | 6/2001 | Benjamin | |
| 2003/0208142 A1* | 11/2003 | Boudewijn et al. | 600/585 |
| 2004/0162559 A1* | 8/2004 | Arramon et al. | 606/62 |

FOREIGN PATENT DOCUMENTS

| | | |
|---|---|---|
| DE | 100 20 739 A1 | 10/2001 |
| DE | 101 38 953 A1 | 2/2003 |
| DE | 696 28 388 T2 | 3/2004 |
| EP | 0 317 091 A2 | 5/1989 |
| EP | 1 004 327 A1 | 5/2000 |

OTHER PUBLICATIONS

German Office Action dated Apr. 26, 2005 (Four (4) Pages).
International Search Report dated Aug. 9, 2005 (Six (6) pages).

* cited by examiner

*Primary Examiner* — Max Hindenburg
*Assistant Examiner* — John Pani
(74) *Attorney, Agent, or Firm* — Crowell & Moring LLP

(57) ABSTRACT

The invention relates to a guide wire for a medical instrument, which has a guide wire core (2) and a sheathing (3) that surrounds the guide wire core at least in sections. According to the invention, the sheathing (3), at least in a shaft section (5) joined to an end section (4), is provided with a rigidity greater than that of the guide wire core. The invention is for use, e.g. in medical instruments for magnetic resonance tomography (MRT) suitable applications.

12 Claims, 7 Drawing Sheets

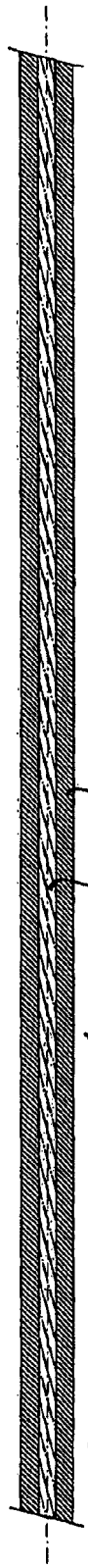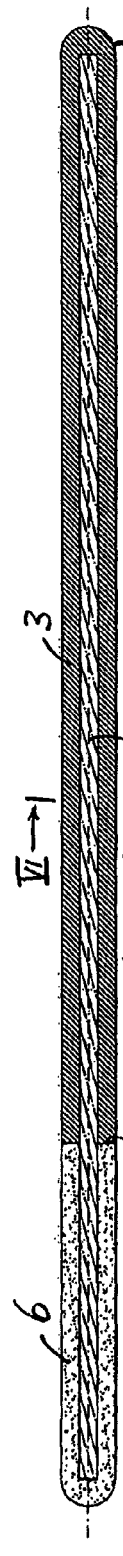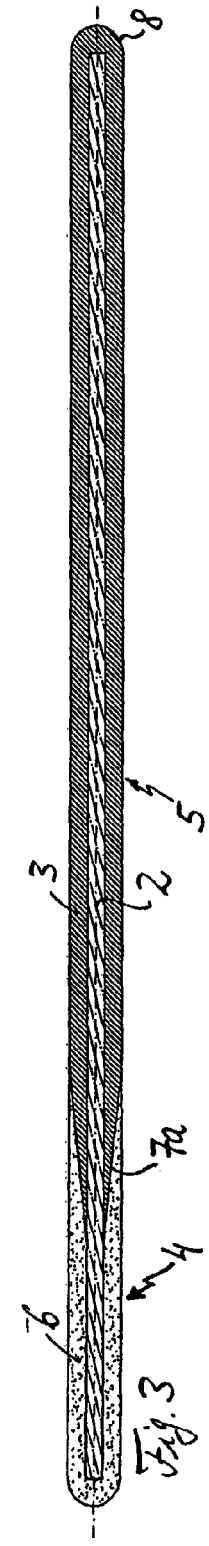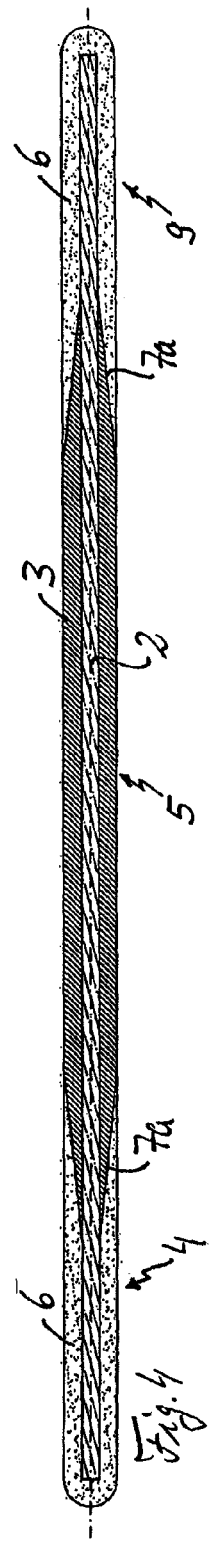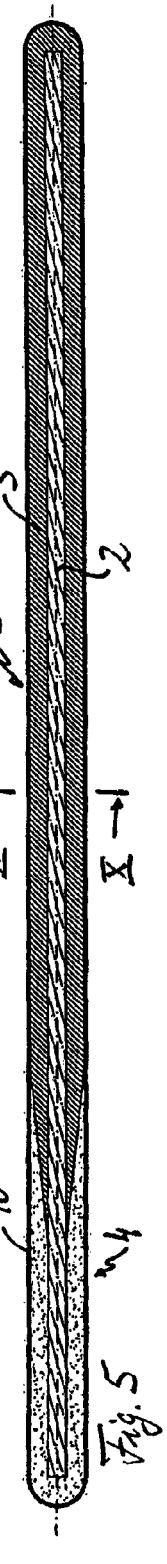

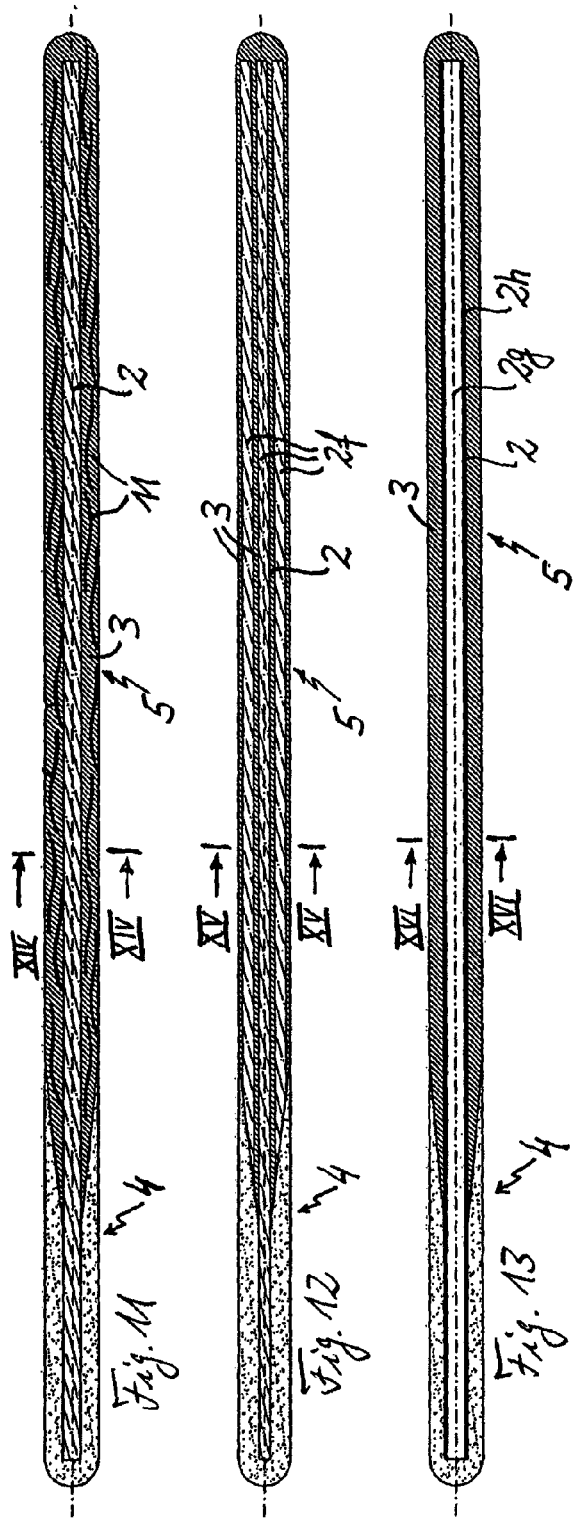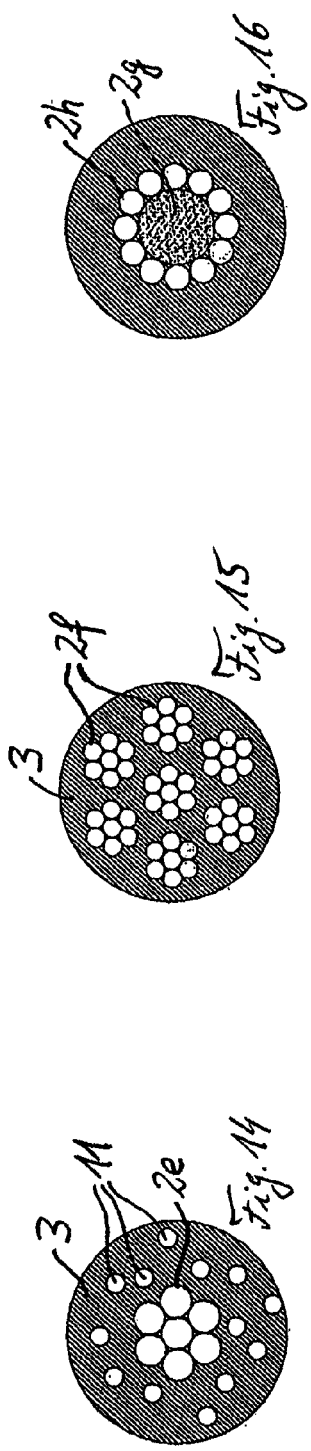

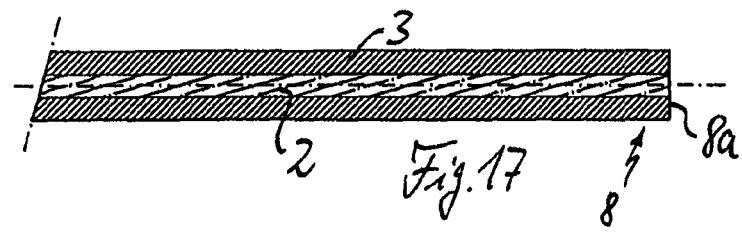
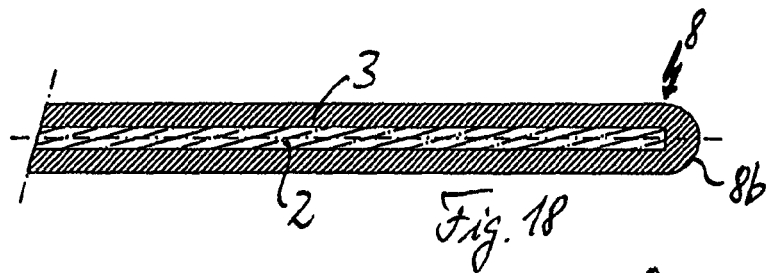
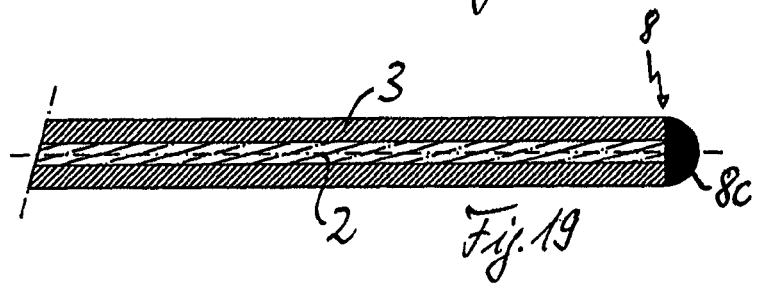
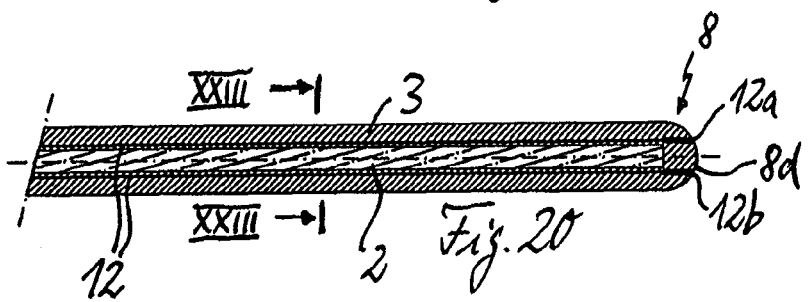
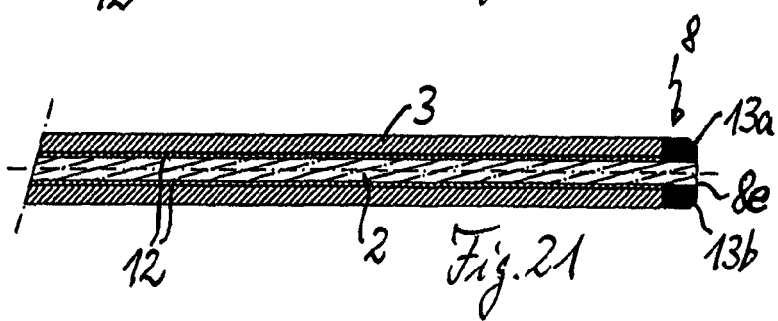
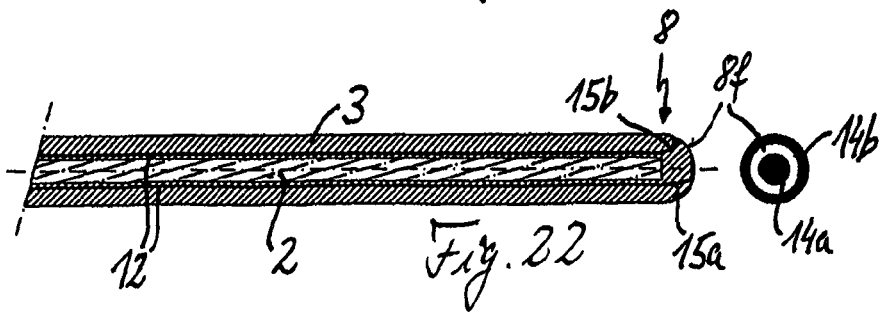

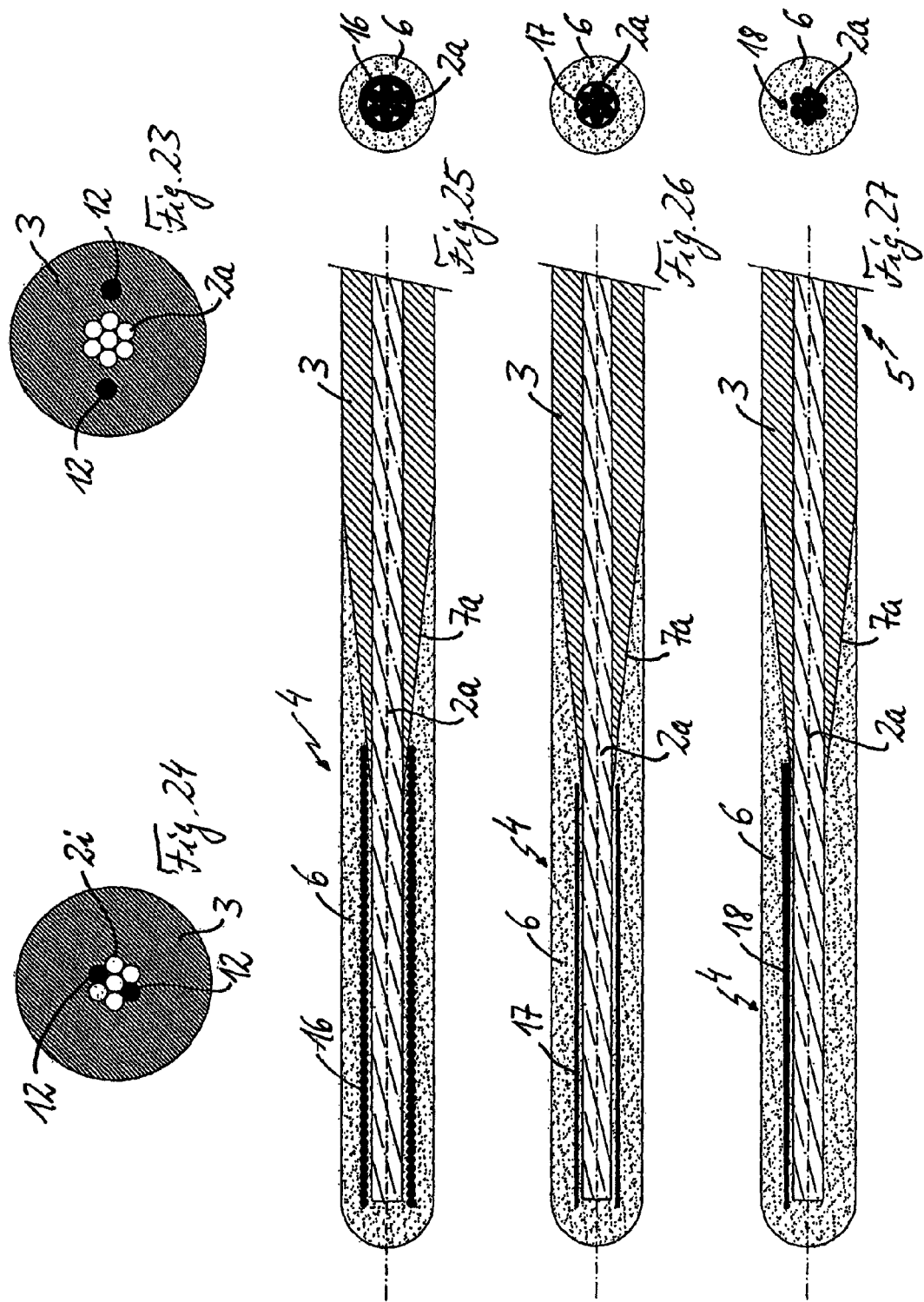

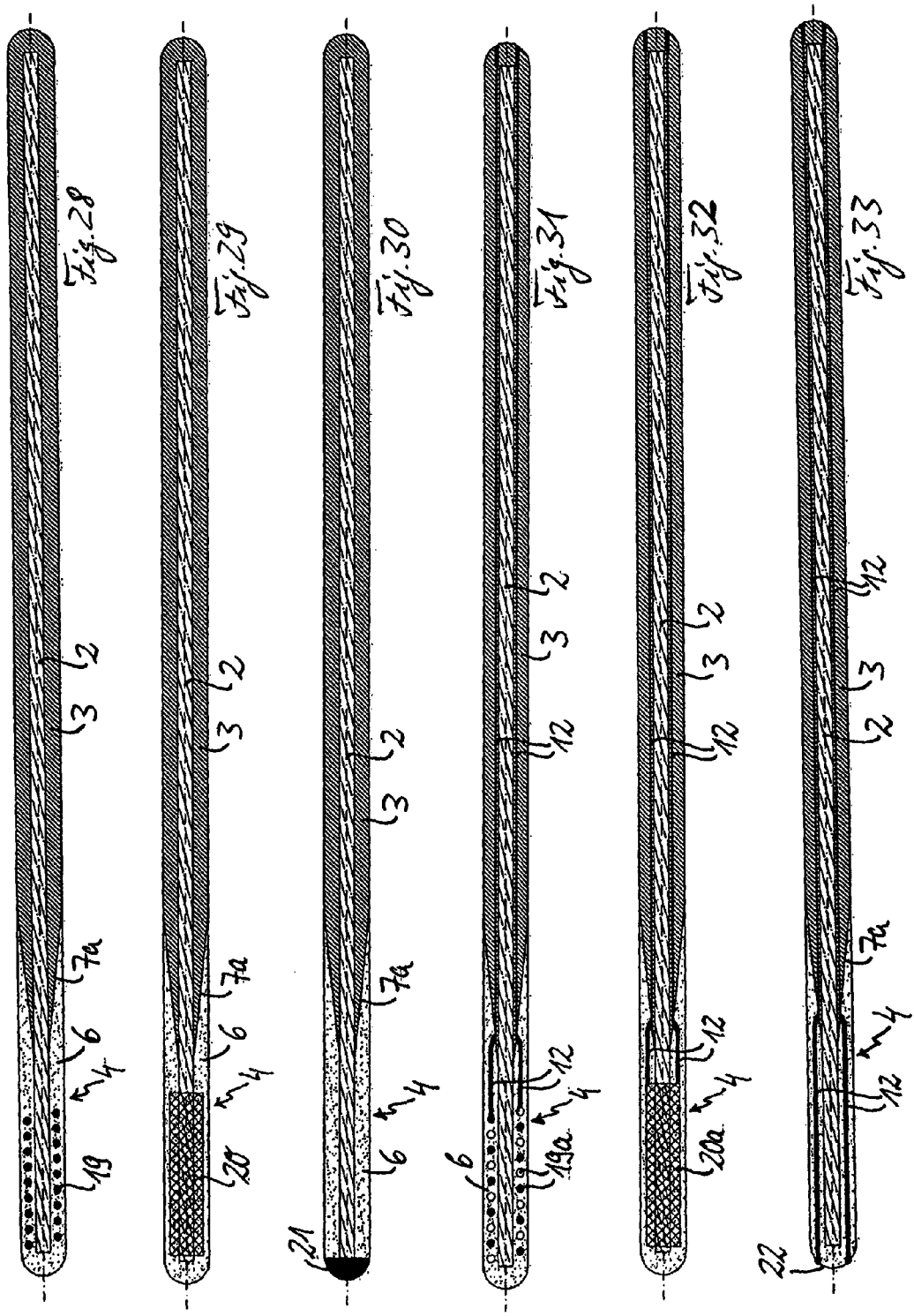

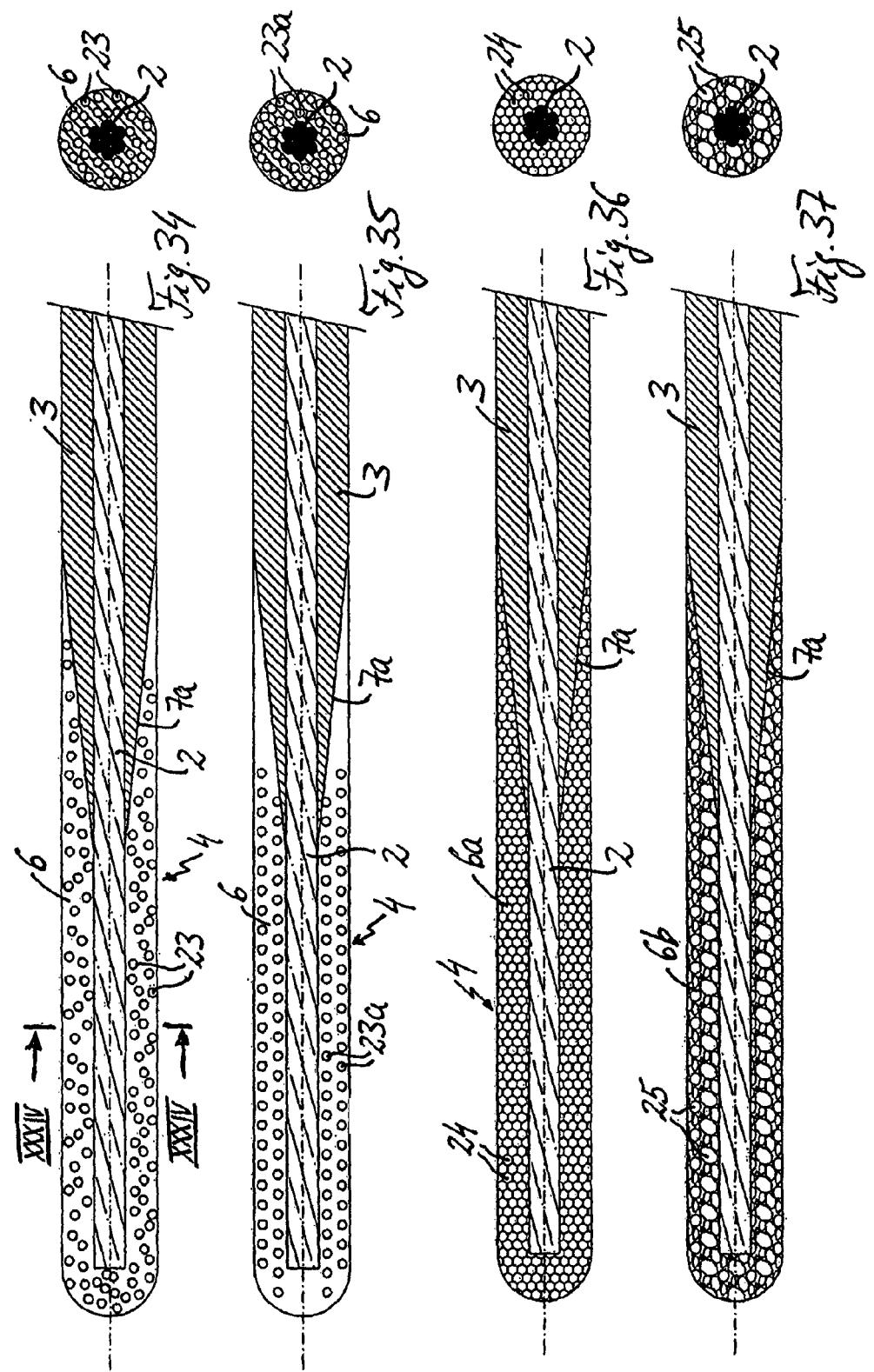

GUIDE WIRE FOR A MEDICAL INSTRUMENT

CROSS REFERENCE TO RELATED APPLICATIONS

This application is a national stage of PCT International Application No. PCT/EP2006/004407 filed May 11, 2006 which claims priority under 35 U.S.C. §119 to German Patent Application No. 10 2005 022 688.4 filed May 12, 2005, the entire disclosures of which are expressly incorporated by reference herein.

BACKGROUND AND SUMMARY OF THE INVENTION

The invention relates to a wire guide for a medical instrument, which has a guide wire core and a sheath which surrounds the guide wire core at least in places, and which is suitable for use, for example, for a medical instrument which is compatible with magnetic resonance imaging, MRI or MR for short, or nuclear magnetic resonance (NMR), and/or examinations with an X-ray application.

In conventional guide wires of this type, the guide wire core, also referred to as the core, is typically used to provide a desired stiffness for the guide wire, while the sheath is typically used to protect the core and/or for application of markings, and is accordingly formed from a material which is more flexible and/or softer than the core. German patent document DE 100 20 739 A1 discloses the specific case of markings which are visible in X-ray radiation.

In this case, it is also known for the guide wire core to taper in a distal, application-end front end section in order for this distal end section to be more flexible than an adjacent shaft section. The tapered core section may likewise be surrounded by a softer sheath or may be designed specifically in some other manner, depending on the requirements. For example, German patent document DE 101 38 953 B4 describes a guide wire with a core which tapers in a distal end section and is surrounded by a helical spring sheath. The spring sheath is connected to the front end of the tapered core via a blunt front end dome.

The invention is based on the technical problem of providing a novel guide wire that can be manufactured with relatively little effort in order to achieve a desired flexibility in at least one end section and a desired stiffness in an adjacent shaft section and, when required, be MRI-compatible and/or compatible with X-ray radiation.

These and other advantages are achieved by a guide wire having a guide wire core and a sheath that surrounds the guide wire core at least in places, wherein the sheath is formed at least in one shaft section, which is adjacent to an end section, with a greater stiffness than the guide wire core.

On the one hand, this allows relatively simple production, for example, from an endless base material composed of two or more different materials for the core and the. On the other hand, this satisfies the precondition of manufacturing at least one end section with a desired flexibility, as required, and in a manner which is simple from the production engineering point of view, as is typically required for guide wires for medical instruments. The one end section preferably has a stiffness which is noticeably less than that of the shaft section. According to one advantageous embodiment, the guide wire can be formed by cutting off the guide wire, for example, from an endless base material with the core and sleeve and removing the sleeve (which, according to the invention, is stiffer than the core) in the relevant end section such that it governs only the greater stiffness of the guide wire in the adjacent shaft section.

The end section with the remaining core may be processed further in some desired manner, for example, by applying a sleeve composed of a different material and/or by fitting one or more further components, depending on the purpose of the guide wire. The flexibility and stiffness of this end section are then not governed, as in the adjacent shaft section, by the sheath which is stiffer than the core, but by the core and/or the component or components which is/are additionally fitted there.

According to one embodiment of the invention, the choice of the material for the core on the one hand and of the sheath on the other hand can be specified independently.

According to a further embodiment of the invention, a distal flexible end section of the guide wire is surrounded by a sleeve whose stiffness is less than that of the sheath in the adjacent shaft section and/or that of the core. This makes it possible to produce the distal end section to be less stiff than the shaft section and accordingly to be more flexible, and at the same time to provide the core with a sleeve which may be matched to the desired purpose. In a further embodiment, an abrupt or continuous transition is provided as required between the sleeve of the distal end section and the sheath of the adjacent shaft section.

In another embodiment of the invention, the guide wire core has one or more individual cores which are distributed over the cross section of the stiffer sheath in the shaft section and are composed of a monofil or multi-fiber material and/or a composite material with a hard-elastic inner core and surrounding fabric material. This allows the stiffness or bending characteristics of the guide wire to be influenced or set in the desired manner according to the purpose in the corresponding section which has the stiffer sheath. By way of example, the stiffness of the shaft section can therefore be varied over a wide range depending on the composition, position and distribution of the individual core or cores and depending on the ratio of the core cross-sectional area to the cross-sectional area of the stiffer sheath.

In yet a further embodiment of the invention, one or more electrical conductors are provided in the core and/or in the sleeve. This makes the guide wire suitable for applications in which electric currents are passed through the guide wire. In a further embodiment, different connection options for the electrical conductors can be provided at the proximal guide wire end.

An MRI and/or X-ray functional unit, which makes the guide wire compatible with MRI and/or X-ray applications, can be provided in the distal end section of the guide wire.

In a further embodiment according to the invention, a spiral structure, a mesh structure, an electrical capacitor structure, an electrical coil structure and/or a separate end dome are/is provided in the distal end section. Components such as these are suitable for specific applications, for example, for providing an MRI function or X-ray visualization for producing electrical and/or magnetic fields and/or for providing sensor elements for measuring pressure, voltage, temperature and other variables.

In a still further embodiment according to the invention, the distal end section of the guide wire is provided with a sleeve that contains a filling material comprising solid or hollow material bodies that are distributed regularly or randomly, or the distal sleeve is provided using a hollow foam material with cavities arranged distributed regularly or randomly. This type of distal sleeve offers the capability to dope the cavities and/or the filling material with a foreign substance in order to set desired magnetic characteristics for the distal end section. By way of example, this may be advantageous for MRI applications.

Finally, according to yet another embodiment according to the invention, a spiral spring surrounding the core, and/or a tubular piece surrounding the core and/or a wire piece running alongside the core are/is provided in the distal end section of the guide wire. Each of the foregoing can act as an element that influences the flexibility of the distal end section such that the flexibility can be set specifically, starting from that of the core, by means of one or more of these elements.

Advantageous embodiments of the invention will be described in the following text and are illustrated in the drawings, in which:

Other objects, advantages and novel features of the present invention will become apparent from the following detailed description of the invention when considered in conjunction with the accompanying drawings.

BRIEF DESCRIPTION OF THE DRAWINGS

FIG. 1 is a longitudinal view, in the form of a detail, of an endless base material for guide wire production, FIG. 2 is a longitudinal sectional view of a guide wire, produced using the endless material shown in FIG. 2, with an abrupt transition from a softer, distal sleeve to a stiffer sheath at the shaft end, FIG. 3 is a view corresponding to FIG. 2 for a guide wire variant with a continuous transition between the distal sleeve and the sheath at the shaft end, FIG. 4 is a view corresponding to FIG. 3 of a variant in which the stiffer sheath is replaced by a softer sleeve in the other end section as well, FIG. 5 is a longitudinal section view corresponding to FIG. 3 for a variant with additional external coating, FIG. 11 is a longitudinal section view corresponding to FIG. 3 for a variant with additional filling material in the shaft-end sheath, FIG. 12 is a longitudinal sectional view corresponding to FIG. 3 of a guide wire variant with a plurality of individual cores, which are arranged distributed over the sheath cross section, of the guide wire core in the shaft area, FIG. 13 is a longitudinal section view corresponding to FIG. 3 of a guide wire variant with a guide wire core composed of composite material.

FIG. 14 is a cross-sectional view along a line XIV-XIV in FIG. 11,

FIG. 15 is a longitudinal sectional view along a line XV-XV in FIG. 12

FIG. 16 is a cross-sectional view along a line XVI-XVI in FIG. 13,

FIG. 17 is a longitudinal section view of a proximal guide wire section with a straight end, FIG. 18 is a longitudinal section view corresponding to FIG. 17 of a variant with a rounded proximal end composed of the sheath material, FIG. 19 is a longitudinal section view corresponding to FIG. 18 for a variant with a proximal end, comprising a rounded end cap composed of additional material, FIG. 20 is a longitudinal sectional view corresponding to FIG. 18 of a guide wire variant having electrical conductors which open out proximally, FIG. 21 is a longitudinal sectional view corresponding to FIG. 20 of a guide wire variant in which the electrical conductors are gripped in a proximal, plug-in connection, FIG. 22 is a longitudinal sectional view corresponding to FIG. 20 of a guide wire variant in which the electrical conductors are passed to proximal end contact surfaces in the left-hand part of the figure, and a plan view of the proximal tip in the right-hand part of the figure, FIG. 23 is a cross-sectional view along a line XXIII-XXIII from FIG. 20, FIG. 24 is a cross-sectional view corresponding to FIG. 23 of a guide wire variant in which the electrical conductors are incorporated in the core rather than in the sheath, FIG. 25 is a longitudinal section view of a distal guide wire end section with a spiral spring surrounding the core in the left-hand part of the figure, and an associated cross-sectional view in the right-hand part of the figure, FIG. 26 is an illustration corresponding to FIG. 25 for a guide wire variant having a tube surrounding the core in the distal end section, FIG. 27 is an illustration corresponding to FIG. 25 for a guide wire variant with a wire piece placed alongside the core in the distal end section, FIG. 28 is a longitudinal sectional view corresponding to FIG. 3 for a guide wire variant with a functional coil in the distal end section, FIG. 29 is a longitudinal sectional view corresponding to FIG. 3 for a guide wire variant with a functional mesh in the distal end section, FIG. 30 is a longitudinal sectional view corresponding to FIG. 3 of a guide wire variant with a functional distal end dome, FIG. 31 is a longitudinal sectional view corresponding to FIG. 28 of a guide wire variant with an electrically connected coil in the distal end section, FIG. 32 is a longitudinal sectional view corresponding to FIG. 29 with an electrically connected capacitor mesh in the distal end section, FIG. 33 is a longitudinal sectional view corresponding to FIG. 3 of a guide wire variant with electrical conductors passing through as far as the distal end tip, FIG. 34 is a cross-sectional view of a distal end section of a guide wire corresponding to FIG. 3 for a variant with MRI-functional filling material balls, which are incorporated in a randomly distributed form in a distal sleeve, in the left-hand part of the figure, and a cross-sectional view along the line XXXIV-XXXIV in the left-hand part of the figure, in the right-hand part of the figure, FIG. 35 is an illustration corresponding to FIG. 34 for a guide wire variant with filling material balls incorporated regularly in the distal sleeve, FIG. 36 is an illustration corresponding to FIG. 34 for a guide wire variant having a distal sleeve composed of a hollow foam material with a regular structure, and FIG. 37 is an illustration corresponding to FIG. 36 for a guide wire variant with a distal sleeve composed of a hollow foam material with an irregular cavity structure.

DETAILED DESCRIPTION OF THE DRAWINGS

Figure 7:
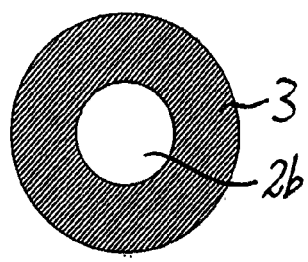

An endless base material composed of two or more different materials can advantageously be used for production of guide wires according to the invention. For example, as shown in the form of a longitudinal section in FIG. 1, the endless material 1 contains a core 2 and a sheath 3 surrounding the core 2. The sheath 3 is characteristically stiffer than the core 2, so that the stiffness of a guide wire produced in this way is governed by that of the sheath 3. For this purpose, the sheath 3 is composed of a material which is stiffer and harder than the core 2, while the core 2 is composed of a tough material, which is softer and more elastic than the material used for the sheath. By way of example, high-quality plastics that are known per se are suitable for use for the sheath 3. Such plastics include polyetheretherketone (PEEK) material or polyimide material, while a plastic material with the same characteristics can likewise be used for the core 2. Alternatively, a metal material can be used as well, for example, a braided wire material composed of stainless steel or NiTi.

FIG. 2 shows a guide wire that can be produced, for example, using the endless material shown in FIG. 1. In a distal end section 4, which is on the left in FIG. 2, and is at the front during use of the guide wire, the guide wire is less stiff than in an adjacent, remaining shaft section 5. Therefore, the distal end is more flexible and it can bend better, as is frequently desired and required during use of guide wires in medical instruments. In the present case, this is achieved by the removal of the sheath 3, which governs the stiffness, from the distal end section 4 of the guide wire, once the desired length of guide wire has been cut off the endless material. Alternatively, it is possible to provide for the required length of the core 2 to be cut off a guide wire core endless material during manufacture of the guide wire, and for this subsequently to be provided with the stiffer sheath only in the shaft section 5. The distal end section of the remaining core 2 is then surrounded by a sleeve 6 which, in the example illustrated in FIG. 2, is abruptly adjacent at a transition point 7 to the sheath 3, which remains in the shaft section 5 and governs the stiffness. The transition point 7 is in this case is located on a transverse plane of the guide wire. Also, in this case, the distal sleeve 6 is smooth on the outside and is aligned with the shaft sheath 3. At the distal tip, the guide wire ends with a rounded end dome that is formed from the same material of the distal sleeve 6.

The distal sleeve 6 is preferably composed of a material that is considerably more flexible than the shaft sheath 3. Furthermore, the distal sleeve 6 is preferably more flexible than the core 2 so that the flexibility of the distal guide wire end section 4 is governed essentially by the length of the core 2 projecting from the shaft sheath 3. At the other, proximal end 8, the guide wire in FIG. 2 is closed by a rounded end dome formed from the same material as the shaft sheath 3.

FIG. 3 shows a variant of the guide wire from FIG. 2, in which the distal sleeve 6 is not abruptly connected to the shaft sheath 3 in the axial direction, but forms a continuous transition 7a. For this purpose, during production, the original sheath 3 is not cut off along a lateral plane as in the example in FIG. 2. Rather, the sheath 3 forms an area which tapers conically in the distal direction from the external diameter of the remaining shaft sleeve to the core 2 where the distal sleeve 6 is once again connected to it and aligned on the outside. This refinement results in a transition which is smoother depending on the axial extent of the transitional area 7a from the higher stiffness of the guide wire shaft 5, governed by the shaft sheath 3, to the greater flexibility of the distal end section 4. It is self-evident that other forms of this transition can also be provided in further alternative embodiments which are not illustrated. For example, a transition can be made in a plurality of steps.

FIG. 4 shows a guide wire variant which differs from the guide wire in FIG. 3 only in that the more flexible configuration of the guide wire end section is provided with a remote hard sheath 3, which remains in the shaft section, and a more flexible sleeve 6, which surrounds the core 2 there, not only in the distal end area 4 but also in an opposite proximal end area 9.

FIG. 5 shows a guide wire variant which corresponds to the guide wire in FIG. 3 but with the entire guide wire additionally being provided on the outside with a coating 10 of a conventional type. Alternatively, the coating may also be provided just in places on the outside of the guide wire, where, in the manner known per se it carries out an intended function, such as sliding capability and/or wear resistance and/or visibility, for example when subjected to X-ray radiation and/or for medicament purposes.

Independently of the rest of the configuration of the guide wire for the respectively intended application, in particular in the distal end section, as shown in the shaft area in the examples in FIGS. 2 to 5, a desired stiffness can be achieved by suitable matching of the nature and material of the core 2 and of the sheath 3 for the area in which the sheath 3 that governs the stiffness remains. FIGS. 6 to 10 show a number of advantageous embodiment variants relating to this.

Figure 6:
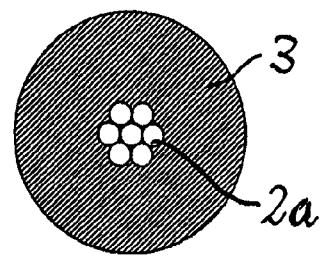
FIG. 6 is a cross-sectional view along a line VI-VI from FIG. 2, FIGS. 7 to 9 are cross-sectional views corresponding to FIG. 6 for further guide wire variants.
Figure 9:
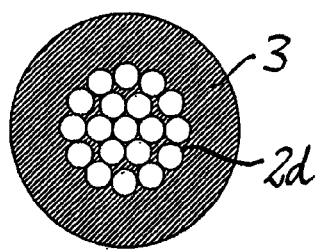
Figure 8:
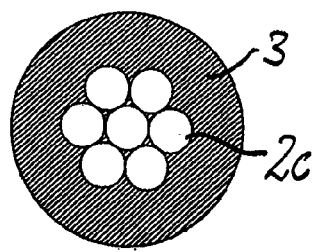
Figure 10:
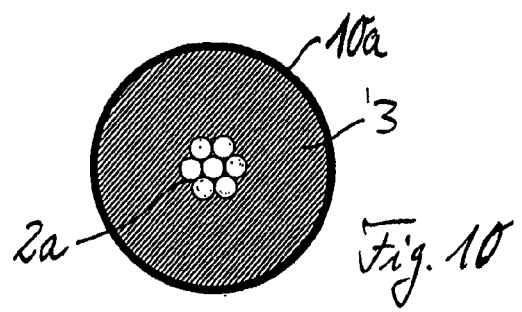
FIG. 10 is a cross-sectional view along a line X-X from FIG. 5.

In the example in FIG. 6, the guide wire core is composed of a braided individual core 2a with a central braid that is surrounded by six braids resting on it. The braided individual core 2a is itself surrounded centrally by the sheath 3. In the example in FIG. 7, the guide wire core is composed of a monofilar individual core 2b, which is once again surrounded centrally by the sheath 3. FIG. 8 shows an exemplary embodiment in which the guide wire core is composed of a braided individual core 2c designed in the same way as the braided individual core 2a in FIG. 6, but as can be seen from FIGS. 6 and 8 the braided individual core 2c in FIG. 8 occupies a larger component of the overall cross section with its cross-sectional area in comparison to the cross-sectional area of the surrounding sheath 3. The relatively small proportion of the cross section of the sheath 3 which governs the stiffness results in the stiffness of the shaft section for the guide wire shown in FIG. 8 being less than that in FIG. 6, assuming the same external diameters. In the exemplary embodiment of FIG. 9, the guide wire core is formed by an even finer-fiber braided individual core 2c whose design corresponds to the braided individual core 2a in FIG. 6 plus a further, radially adjacent layer of twelve surrounding individual braids, once again being centrally surrounded by the sheath 3. In the example in FIG. 10, the guide wire core is composed of the braided individual core 2a as shown in FIG. 6 surrounded by the sheath 3, with the stiffness in this case being additionally influenced by a corresponding coating 10a in the same form as the coating 10 on the guide wire in FIG. 5.

As can clearly be seen from FIGS. 6 to 9, there are various options of monofilar to fine-fiber configurations that can be used to produce a desired tough, tear-resistant central core. Further variants are illustrated in FIGS. 11 to 16. For example, FIGS. 11 and 14 show a guide wire which in general corresponds to that in FIG. 3 in which the shaft section 5, which bends less easily, has a central braided individual core 2e of the same form as that in FIG. 8, but with an additional filling material 11 being incorporated in the sleeve 3 in order to set a desired stiffness. The filling material 11 may, for example, be fiber reinforcement for the sheath material 3.

FIGS. 12 and 15 show a guide wire which in general corresponds to that in FIG. 3, in which the guide wire core in the shaft section 5 comprises a plurality of braided individual cores 2f whose design in each case corresponds to that of the braided individual core 2a in FIG. 6, with one core being embedded in the sheath 3 centrally, and six further cores being embedded uniformly in the circumferential direction, between the central core and the guide wire outer circumference.

FIGS. 13 and 16 show a guide wire which otherwise corresponds to FIG. 3, in which the guide wire core 2 is composed of a composite material with a hard elastic inner wire 2g, for example composed of a carbon-fiber-reinforced plastic material (CFRP) and a surrounding, tough, high breaking strength fabric 2h, for example composed of para-aramid fiber material, such as the brand name KEVLAR material. Alternatively, the para-aramid fiber material can also be used for the inner wire 2g, and this may have advantages in guide wire production, because of the high melting point of this material.

FIGS. 17 to 22 show variants of the guide wire configuration at the proximal end 8. In the situation shown in FIG. 17, the guide wire ends simply in a form cut off from an endless material and is not processed any further. FIG. 18 shows the variant already discussed above with reference to FIG. 2 with a rounded proximal end tip 8b composed of the same material as the sheath 3. FIG. 19 shows a variant with a rounded proximal end dome 8c that is fitted and composed of a separate material. Since the material of the end dome 8c can be chosen independently from the sheath material, the proximal end dome 8c can be designed for a specific functional characteristic, as required.

FIGS. 20 to 22 show different options for a proximal guide wire termination with which electrical contact can be made. In these exemplary embodiments, the guide wire has at least two longitudinally running electrical conductors 12 via which electric currents can be passed, during use of the guide wire between the distal and the proximal guide wire end section. In the example in FIG. 20, the electrical conductors 12 open separately, corresponding to the distance between them in the guide wire, with in each case one conductor end 12a, 12b adjacent to a rounded proximal end dome 8d. In the example shown in FIG. 21, the guide wire is provided with a proximal end termination 8e that provides in each case one electrical contact area 13a, 13b to which the relevant electrical conductor 12 is electrically connected, for each electrical conductor 12. This proximal end termination 8e forms a type of electrical plug connection via which the guide wire, and therefore specifically its electrical conductor 12, can be contacted with at its proximal end. In the example in FIG. 22, a rounded proximal end dome 8f composed of the sheath material is provided. On the outside of the end dome, a central point contact surface 14a is provided having an annular contact surface 14b surrounding at a distance. In each case, one electrical conductor can be connected thereto from the outside, for example by soldering or by an appropriate plug contact. One of the electrical conductors 12 in the guide wire has a proximal end section 15a that is guided to the central point contact surface 14a and makes contact with it, or a further one of the electrical conductors 12 is guided by its proximal end section 15b to the annular contact surface 14b, and makes contact with it.

FIG. 23 shows a cross section through the guide wire in FIG. 20, clearly showing that this guide wire is designed in its shaft section in the way shown in FIG. 6, with the two electrical conductors additionally running on opposite sides and at a certain distance from the central braided individual core 2a in the interior of the sheath 3. In an alternative embodiment, as shown in FIG. 24, for the guide wire core, a modified braided individual core 2i having one central braid and six surrounding braids is used, two of which braids, which are positioned on opposite sides of the central braid, are in the form of the two electrical conductors 12. It is self-evident in this case that the other braids of this braided individual core 2i are composed of an electrically insulating material, or electrically insulate the individual braids from one another. It is also self-evident that mixed forms of the examples shown in FIGS. 23 and 24 are also possible, that is to say embodiments in which some of the electrical conductors are incorporated in the core, and the rest are incorporated in the sheath.

If required, additional measures can be provided for the distal end section of guide wires according to the invention in order to achieve a desired flexibility, different options relating to which are illustrated by way of example in FIGS. 25 to 27. For example, in the case of a guide wire in FIG. 25, which otherwise corresponds to that in FIG. 3, the guide wire core, which in this case is once again composed, for example, of the braided individual core 2a, is surrounded by its distal end section, from which the stiff sheath 3 has been removed, by a spiral spring 16 with a predeterminable, defined flexibility. The spiral spring 16 in governs the flexibility of the distal end section 4 by reducing the flexibility in a desired manner, starting from that of the core 2a. During manufacture of the guide wire, the spiral spring 16 is fitted with the distal wire core end before the distal sleeve 6 is fitted, and is then completely embedded by the distal sleeve 6 that is fitted.

FIG. 26 shows a variant of FIG. 25, in which, as the only difference, a thin-walled tube 17 instead of the helical spring 16, is pushed onto the distal end area of the core 2a in order to set a desired flexibility or resilience of the distal guide wire end section 4. In the illustrated example, the tube 17 is cylindrical with a uniform wall thickness. In alternative embodiments, which are not shown, a conically ground tube or a laser-cut tube is used in order to deliberately influence the flexibility, for example, a flexibility which gradually increases in the direction of the distal tip as a result of a gradually decreasing tube wall thickness of an appropriately conically ground tube.

FIG. 27 shows a guide wire variant in which the only difference from the exemplary embodiment in FIG. 26 is an individual wire piece 18 as the element which governs the flexibility being incorporated in the distal end section 4, at a certain distance away from and alongside the central core 2a. As can be seen in particular from the left-hand part of the figure, this wire piece 18 in the illustrated example is ground conically with a wire diameter which decreases in the direction of the distal guide wire tip. This results in the flexibility of the distal end section 4 increasing gradually towards the distal tip. In combination with the gradual increase in the flexibility in the transitional area 7a from the relatively stiff shaft sheath 3 to the distal end area 4, a termination of the shaft sheath 3, which in this case tapers conically, results in a comparatively smooth transition between the relatively low flexibility of the guide wire shaft 5 and the relatively flexible distal tip area of the guide wire.

In principle, any desired flexible materials may be used for the additional elements 16, 17, 18 which influence the flexibility, in particular including those which are compatible with MRI applications, such as high-strength plastics and Nitinol. Stainless steel is also a preferred material. Together with the material-specific elasticity and flexibility of the core 2 and of the distal sleeve 6, which may optionally also include an additional filling material, the additional elements which influence the flexibility make it possible to set any desired flexibility of the distal guide wire end section 4.

The guide wire configuration according to the invention also advantageously makes it possible, if required, to design the distal end section, for example, specifically for MRI applications, or else for applications involving X-ray radiation observation or for applications with sensor functions. By way of example, a number of embodiments relating to this are shown in FIGS. 28 to 37.

In the case of the guide wire in FIG. 28, which otherwise corresponds to that in FIG. 3, the core 2 is surrounded by a coil 19 in its distal end area from which the sheath 3 has been removed. This makes it possible to improve the required characteristics for MRI or X-ray radiation applications. This also applies to a mesh 20 which, in the case of the guide wire in FIG. 29, is incorporated in the distal end section 4 instead of the coil 19, with the guide wire configuration otherwise being identical to that in FIG. 28. In the case of the guide wire variant shown in FIG. 30, which otherwise corresponds to that in FIG. 3, the distal tip is formed by a rounded end dome 21 composed of an additional material, which is chosen in order to improve a desired characteristic for MRI or X-ray radiation applications.

FIG. 31 shows an embodiment of the type shown in FIG. 3, both with electrical conductors 12 additionally passed through, which open at the proximal end in the way shown in FIG. 20, and are passed distally to a coil 19a and make contact with it. Like the coil 19 in FIG. 28, the coil 19a surrounds the core 2 in the distal end section 4, embedded in the distal sleeve 6. In this example, however, the coil 19a can have current passing through from the proximal guide wire end via the electrical conductors 12, as a result of which the current flow in the coil 19a makes it possible to produce a magnetic field in the distal guide wire end section 4.

FIG. 32 shows a guide wire variant which, as the only difference from the guide wire shown in FIG. 31, has a capacitor mesh 20a in the distal guide wire end section 4, rather than the coil 19a. The capacitor mesh 20a design may correspond to that of the mesh 20 in FIG. 29, and current can be passed through from the proximal guide wire end via the electrical conductors 12 in this case, thus allowing it to act as an electrical capacitor. It is self-evident that the mesh 20a for this purpose forms two electrically isolated capacitor electrodes, which each make contact with one of the two electrical conductors 12. In consequence, an electrical field or potential can be produced in the distal guide wire end section 4 by passing current through the capacitor mesh 20a.

In a guide wire variant which is shown in FIG. 33, and otherwise corresponds to that shown in FIG. 3, the electrical conductors 12 are additionally provided in the manner shown in FIG. 20, and in this case are passed as far as the distal end tip 22 of the guide wire. This embodiment variant, with respect to the electrical conductors 12 may, for example, be used for sensor applications such as pressure, voltage and/or temperature measurements.

Especially for MRI applications and similar applications, as an alternative or in addition to the measures explained above, which include the incorporation of functional additional elements, appropriate designs of the distal sleeve are also advantageous for certain cases. Some exemplary embodiments relating to this are illustrated in FIGS. 34 to 37.

FIG. 34 shows an exemplary embodiment in which the distal sleeve 6 includes a filling material 23 composed of irregular, i.e., chaotically arranged small balls 23, which may be solid balls or hollow balls. In the case of a filling material such as this, the small balls 23, and other filling bodies that are used, act as resonant bodies in the magnetic fields of MRI applications. The magnetic fields in MRI applications are highly dependent on the shape and position of the filling-material bodies. The incorporation of filling material balls 23 can improve the MRI compatibility and the MRI characteristics, especially of the distal functional end section 4 of the guide wire. Apart from this, the guide wire in FIG. 34 may, for example, correspond to that shown in FIG. 3.

FIG. 35 shows a guide wire variant which otherwise corresponds to that in FIG. 34 and in which a filling material which contains a regular arrangement of filling balls 23a is incorporated in the distal sleeve 6. Specifically, the filling balls 23a in this example are arranged coaxially around the central core 2 in two layers that are radially separated from one another. Apart from this, the characteristics and advantages for the guide wire as explained above with reference to FIG. 34 apply in a corresponding manner to the guide wire in FIG. 35.

FIG. 36 shows a guide wire variant in which the distal sleeve is formed by a hollow foam structure 6a. A structured foam material that is known per se may be used for the sleeve. The hollow foam structure 6a contains honeycomb hollow bodies 24 which, together with the surrounding foam material, can act as resonant bodies for MRI applications. In the example illustrated in FIG. 36, the hollow honeycomb bodies 24 are arranged in a regular pattern. In a variant shown in FIG. 37, the distal sleeve is formed by a hollow foam structure 6b with an irregular, chaotic distribution of cavities 25. In this case, the shapes and sizes of the hollow bodies 25 also vary, such that, together with the foam material surrounding them, they can once again act as resonant bodies in MRI applications.

In further unillustrated variants of the exemplary embodiments relating to FIGS. 36 and 37, the cavities 24, 25 in the structure foam material, which forms the distal sleeve, are deliberately doped with suitable foreign substances, for example, they are filled with suitable foreign gases that change the magnetic characteristics of the distal sleeve 6a, 6b in a desired manner in order to produce specific MRI-compatible characteristics.

As the exemplary embodiments described above make clear, the invention makes it possible to produce guide wires with relatively little manufacturing effort, which are MRI-compatible as and/or are suitable for applications involving X-ray radiation observation. In this case, the stiffness of the guide wire, at least in a shaft section adjacent to an end section, is characteristically governed by a sheath that is stiffer than the core. If required, this stiffer sheath may be omitted in an end section, for example, a distal end section of the guide wire unless it is not fitted from the start in this area over the core, or is removed from the core in this area, for example when using an endless material. The flexibility of the end section from which the stiff sheath has been removed can then be set as desired, if necessary by appropriate additional measures. Since the core need not be designed to provide adequate guide wire stiffness in the shaft section, with this function in fact being carried out by the stiffer sheath, it can be chosen to be more flexible and less stiff. It is therefore not absolutely essential for the core to taper in this area in order to achieve a high bending capability and high flexibility of the distal guide wire end section. Furthermore, this guide wire configuration according to the invention makes it possible to optimize free spaces, for example the distal guide wire end section, for MRI applications and similar known guide wire applications in medical instruments.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A guide wire for a medical instrument, comprising:
   a guide wire core composed of a core material extending with a same cross-sectional area in a shaft section and a distal section adjacent the shaft section, said core material comprising at least one of a group consisting of stainless-steel, NiTi, para-aramid fiber materials, multi-fiber materials, and composite materials having a hard-elastic inner core and surrounding fabric material;
   a shaft sheath composed of a plastics material different from the core material and surrounding the guide wire core in the shaft section at least in places; and
   a distal sleeve composed of a plastics material different from the core material and the shaft sheath material and surrounding the guide wire core in the distal section at least in places, wherein the shaft sheath has a greater stiffness than the guide wire core and the distal sleeve.

2. The guide wire as claimed in claim 1, wherein the shaft sheath is composed of a polyetheretherketone material or polyimide material and/or contains filling material.

3. The guide wire as claimed in claim 1, wherein a transition between the distal sleeve and the shaft sheath is an abrupt transition or a continuous transition in a longitudinal direction of the guide wire.

4. The guide wire as claimed in claim 1, wherein the guide wire core has one or more individual cores which are distributed over the cross section of at least the shaft sheath in the shaft section and are composed of a multi-fiber material or a composite material with a hard-elastic inner core and surrounding fabric material.

5. The guide wire as claimed in claim 1, further comprising one or more electrical conductors which run along the guide wire core and/or in the shaft sheath.

6. The guide wire as claimed in claim 5, wherein the one or more electrical conductors open out at a proximal guide wire end and are gripped in a plug connection or are connected to separate contact surfaces.

7. The guide wire as claimed in claim 1, further comprising a magnetic resonance imaging and/or X-ray functional unit in a distal end section.

8. The guide wire as claimed in claim 1, further comprising at least one of: a coil, a mesh, a separate end dome, an electrical coil structure and an electrical capacitor structure in a distal end section.

9. The guide wire as claimed in claim 1, wherein the distal sleeve contains a filling material with filling bodies which are distributed regularly or randomly or is formed from a hollow-foam material with cavities which are distributed regularly or randomly.

10. The guide wire as claimed in claim 9, wherein at least one of the filling bodies and the cavities are doped with foreign substances in order to set predeterminable magnetic characteristics.

11. The guide wire as claimed in claim 1, wherein a distal end section includes one or more of an element which influences flexibility and is in the form of at least one of a spiral spring surrounding the guide wire core, a tubular piece surrounding the guide wire core, and a wire piece running alongside the guide wire core.

12. The guide wire as claimed in claim 1, wherein a transition between the distal sleeve and the shaft sheath is a continuous transition having a defined axial length in a longitudinal direction of the guide wire and is not an abrupt transition.

* * * * *